US012742186B2

(12) United States Patent
Znameroski et al.

(10) Patent No.: US 12,742,186 B2
(45) Date of Patent: Sep. 22, 2026

(54) CULTURE COMPOSITIONS AND METHODS OF THEIR USE FOR HIGH YIELD PRODUCTION OF VANILLIN

(71) Applicant: AMYRIS, INC., Emeryville, CA (US)

(72) Inventors: Elizabeth Znameroski, Emeryville, CA (US); Yi-Shu Tai, Emeryville, CA (US); Lauren Raetz, Emeryville, CA (US); Abhishek Murarka, Emeryville, CA (US); Brandon Friedrikson, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 681 days.

(21) Appl. No.: 18/245,450

(22) PCT Filed: Sep. 15, 2021

(86) PCT No.: PCT/US2021/050506
§ 371 (c)(1),
(2) Date: Mar. 15, 2023

(87) PCT Pub. No.: WO2022/060867
PCT Pub. Date: Mar. 24, 2022

(65) Prior Publication Data

US 2024/0026390 A1 Jan. 25, 2024

Related U.S. Application Data

(60) Provisional application No. 63/078,841, filed on Sep. 15, 2020.

(51) Int. Cl.

*C12P 7/24* (2006.01)
*C12N 9/02* (2006.01)
*C12N 9/10* (2006.01)
*C12N 9/12* (2006.01)
*C12N 9/88* (2006.01)
*C12N 15/52* (2006.01)

(52) U.S. Cl.

CPC .............. *C12P 7/24* (2013.01); *C12N 9/0008* (2013.01); *C12N 9/1007* (2013.01); *C12N 9/1051* (2013.01); *C12N 9/1085* (2013.01); *C12N 9/1288* (2013.01); *C12N 9/88* (2013.01); *C12N 15/52* (2013.01); *C12Y 102/0103* (2013.01); *C12Y 204/01126* (2013.01); *C12Y 205/01054* (2013.01); *C12Y 207/08007* (2013.01); *C12Y 402/0101* (2013.01); *C12Y 402/01118* (2013.01); *C12Y 402/03004* (2013.01)

(58) Field of Classification Search

None
See application file for complete search history.

(56) References Cited

U.S. PATENT DOCUMENTS

| | | | | |
|---|---|---|---|---|
| 6,372,461 B1 | 4/2002 | Frost | | |
| 10,066,252 B1 | 9/2018 | Hansen et al. | | |
| 2016/0153016 A1* | 6/2016 | Hansen | C12N 9/0006 435/254.2 | |
| 2016/0177341 A1* | 6/2016 | Chua | C12N 15/81 435/254.2 | |
| 2022/0282226 A1* | 9/2022 | Raetz | C12P 19/46 | |

FOREIGN PATENT DOCUMENTS

| | | | |
|---|---|---|---|
| EP | 2749644 A1 * | 7/2014 | C12P 7/24 |
| WO | WO 00/50622 A1 | 8/2000 | |

OTHER PUBLICATIONS

SC Complete Powder, Sunrise Science Products, 2018. (Year: 2018).*

Li et al., De novo production of resveratrol from glucose or ethanol by engineered *Saccharomyces cerevisiae*, Metabolic Eng. 32, 2015, 1-11. (Year: 2015).*

Shi et al., A highly efficient single-step, marker less strategy for multi-copy chromosomal integration of large biochemical pathways in *Saccharomyces cerevisiae*, Metabolic Eng. 33, 2016, 19-27. (Year: 2016).*

Stokes et al., Vitamin content of ingredients of microbiological culture media, J. Bacteriology 47, 1944, 293-9. (Year: 1944).*

Averesch et al., Production of para-aminobenzoic acid from different carbon-sources in engineered *Saccharomyces cerevisiae*, Microb. Cell Fact. 15, 2016, 89. (Year: 2016).*

Gientka et al., p-Aminobenzoic acid (PABA) changes folate content in cell biomass of *Saccharomyces cerevisiae*, Polish J. Food Nutrition Sci. 60, 2010, 13-17. (Year: 2010).*

International search report and written opinion of PCT/US2021/050506 mailed Jan. 13, 2022; 11 pages.

Gallage et al., "Vanillin -bioconversion and bioengineering of the most popular plant flavor and its de novo biosynthesis in the vanilla orchid", Molecular Plant, vol. 8, Jan. 1, 2015, pp. 40-57, XP002778912.

Hansen, E.H. et al., "De Novo Biosynthesis of Vanillin in Fission Yeast (*Schizosaccharomyces pombe*) and Baker's Yeast (*Saccharomyces cer evisiae*)", Applied and Environmental Microbiology, May 2009, vol. 75, No. 9 pp. 2765-2774; doi:10.1128/AEM.02681-08.

* cited by examiner

*Primary Examiner* — Todd M Epstein

(74) *Attorney, Agent, or Firm* — Squire Patton Boggs (US) LLP

(57) ABSTRACT

Provided herein are fermentation compositions and methods for improved production of vanillin and/or glucovanillin. The compositions and methods described herein provide efficient routes for the production of vanillin and/or glucovanillin and any compound that can be synthesized or biosynthesized from either or both.

14 Claims, 3 Drawing Sheets vanillin normalized to standard concentration pABA

CULTURE COMPOSITIONS AND METHODS OF THEIR USE FOR HIGH YIELD PRODUCTION OF VANILLIN

This application claims benefit of priority of U.S. Provisional Application No. 63/078,841, filed on Sep. 15, 2020, the contents of which are hereby incorporated by reference in their entirety.

FIELD OF THE INVENTION

The present disclosure relates to fermentation compositions and methods of their use for the production of vanillin and/or glucovanillin and any compound that can be synthesized or biosynthesized from either or both.

BACKGROUND

Vanillin is the largest-volume flavor ingredient in the world. Only about 1% of the vanilla flavor ingredient supply comes from vanilla extract from the vanilla orchid. There is strong demand, insufficient supply, and a high price for "natural" vanillin. An alternative, low cost, high-volume source of "natural" vanillin would be a lucrative addition to the flavorings market. Vanillin produced de novo through fermentation of sugar by yeast has the potential to generate "natural" vanillin at a lower cost than alternatives currently in the market.

There are several approaches that are being used to generate "natural" vanillin by bioconversion from natural precursors, including precursors other than glucose. One path is bioconversion of ferulic acid which is found abundantly in certain parts of certain plants. Microorganisms have been identified which catabolize ferulic acid by a pathway which generates vanillin as an intermediate. These microorganisms can be engineered to reduce further catabolism of vanillin to unwanted side products to optimize vanillin production. Gallage et al., *Molecular Plant,* 8: 40-57 (2015). In a similar approach, the more cost-effective substrate eugenol can be catabolized by microorganisms to ferulic acid and further to vanillin. Gallage et al.

There is no known microorganism that can natively convert glucose to vanillin. Gallage et al. In 1998, an enzymatic route from glucose to vanillin was developed which converts a natively produced metabolite 3-dehydroshikimate into vanillin with three additional enzymatic steps: 1) dehydration to produce protocatechuic acid (3,4-dihydroxybenzoic acid), 2) O-methylation of the 3-hydroxyl group, and 3) reduction of the carboxylic acid to an aldehyde. Li and Frost, *J. Am. Chem. Soc.,* 120: 10545-10546 (1998). This process was demonstrated by producing vanillic acid (steps 1 and 2) in *E. coli* by expression of heterologous enzymes catalyzing 3-DHS dehydratase (AroZ) and catechol-O-methyltransferase (COMT). An enzymatic conversion using an aromatic carboxylic acid reductase (ACAR) purified from fungi was used to convert vanillic acid to vanillin in vitro.

Hansen et al. demonstrated de novo biosynthesis of vanillin from glucose in a single recombinant organism, *Saccharomyces cerevisiae*, by expressing the above enzymes in combination with a heterologous PPTase, which was identified to be necessary to activate the ACAR enzyme in this organism. Hansen et al., *Appl. Environ. Microbiol.* 75:2765-2774 (2009). In addition, they expressed a UDP-glucosyltransferase to convert the toxic vanillin product into the far less toxic glucovanillin.

A number of other modifications have been reported to improve the efficiency of vanillin biosynthesis in yeast. In order to improve titer of glucovanillin, Hansen et al. demonstrated that it was important to reduce endogenous reductase activity through the deletion of native reductases (i.e. ADH6) to reduce conversion of vanillin to vanillyl alcohol, and to eliminate native β-glucosidase activity by deleting EXG1 to reduce hydrolysis of the glucose moiety during fermentation. In subsequent filings, the use of a vanillyl alcohol oxidase was reported to further mitigate the loss of carbon from reduction of vanillin to vanillyl alcohol. US2014/0245496 A1; WO 2015 121379 A2. In order to mitigate loss of carbon to the undesired isomer, isovanillin (produced by methylation of the 4-OH instead of 3-OH), the human variant Hs.COMT was used as a starting point for enzyme evolution. Mutants were obtained which were highly specific for the correct vanillin isomer. In order to increase flux to protocatechuic acid (PCA) and reduce flux to shikimate pathway metabolites, a mutant version of Aro1 (referred to as AROM) was generated having a mutation in the E domain that confers reduced activity of the shikimate reaction using 3-DHS as a substrate.

Accordingly, further genetic modifications that can provide low cost, high-volume sources of "natural" vanillin would be a significant addition to the flavorings market.

SUMMARY OF THE INVENTION

Provided herein are compositions and methods for the improved production of vanillin and/or glucovanillin. These compositions and methods are based in part on the discovery of a nutrient p-aminobenzoic acid that is capable of promoting vanillin and/or glucovanillin production from certain cell strains. While not intending to be bound by any particular theory of operation, the examples herein demonstrate that increasing p-aminobenzoic acid in culture improves the yield and productivity of vanillin or glucovanillin production.

In one aspect, provided herein are fermentation compositions comprising one or more yeast strains capable of producing vanillin or glucovanillin and an increased amount of p-aminobenzoic acid compared to conventional yeast fermentation compositions. Useful amounts of p-aminobenzoic acid are described herein. In particular embodiments, the fermentation compositions further comprise nutrients, minerals, vitamins, and carbon sources suitable for growth of the yeast strains and suitable for the production of vanillin or glucovanillin.

In another aspect, provided herein are methods for producing vanillin or glucovanillin involving: culturing a population of the cell strains described herein in a medium with an increased amount of p-aminobenzoic acid under conditions suitable for making vanillin or glucovanillin to yield a culture broth; and recovering the vanillin or glucovanillin from the culture broth.

In a further aspect, provided herein is vanillin or glucovanillin produced by a method provided herein.

The compositions and methods are useful for producing vanillin and/or glucovanillin for any purpose, including as flavorings and food ingredients. They are also useful for producing any compound that can be synthesized or biosynthesized from vanillin and/or glucovanillin. The compounds can be produced synthetically, or biosynthetically with downstream enzymes or pathways, or a combination thereof. Such compounds include vanillic acid, vanillyl alcohol, ferulic acid, eugenol, and heliotropin.

DETAILED DESCRIPTION OF THE EMBODIMENTS

Terminology

Figure 1:
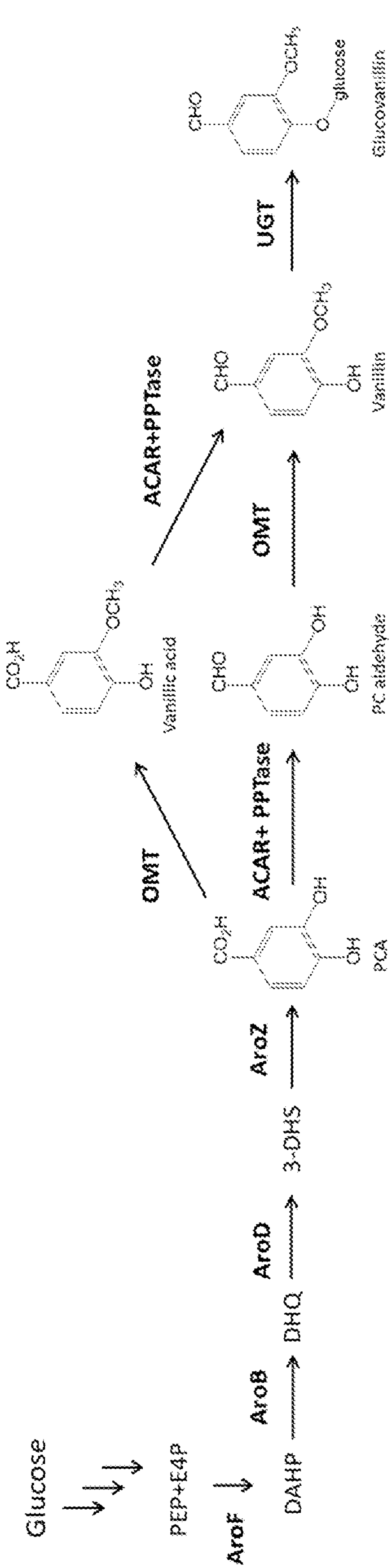
FIG. 1 is a schematic showing an enzymatic pathway from glucose to vanillin and glucovanillin.

As used herein, the term "about" refers to a reasonable range about a value as determined by the practitioner of skill. In certain embodiments, the term about refers to ±one, two, or three standard deviations. In certain embodiments, the term about refers to ±5%, 10%, 20%, or 25%. In certain embodiments, the term about refers to ±0.1, 0.2, or 0.3 logarithmic units, e.g. pH units.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its cell strain (i.e., is "exogenous" to the cell); (b) naturally found in the cell strain (i.e., "endogenous") but present at an unnatural quantity in the cell (i.e., greater or lesser quantity than naturally found in the cell strain); or (c) be naturally found in the cell strain but positioned outside of its natural locus. The heterologous nucleotide sequence and expressed protein may be referred to as "recombinant."

On the other hand, the term "native" or "endogenous" as used herein with reference to molecules, and in particular enzymes and nucleic acids, indicates molecules that are expressed in the organism in which they originated or are found in nature. It is understood that expression of native enzymes or polynucleotides may be modified in recombinant microorganisms. In particular embodiments, codon optimized genes express native enzymes.

As used herein, the term "heterologous nucleic acid expression cassette" refers to a nucleic acid sequence that comprises a coding sequence operably linked to one or more regulatory elements sufficient to expresses the coding sequence in a cell strain. Non-limiting examples of regulatory elements include promoters, enhancers, silencers, terminators, and poly-A signals.

As used herein, gene names are typically presented in all capitals and italicized, e.g. HFD1. Protein names are typically initially (first letter) capitalized and not italicized, e.g. Hfd1 or Hfd1p. However, where the term protein is indicated, then the protein is intended. For instance, those of skill will recognize that "HFD1 protein" is intended to refer to Hfd1p.

As used herein, the terms "homolog of fatty aldehyde dehydrogenase" and "HFD1" or "Hfd1" refer to an encoding nucleic acid and a dehydrogenase involved in ubiquinone and sphingolipid metabolism capable of converting 4-hydroxybenzaldehyde into 4-hydroxybenzoate for ubiquinone anabolism and/or hexadecenal to hexadecenoic acid in sphingosine 1-phosphate catabolism. In certain embodiments, its EC number is 1.2.1.3. In certain embodiments, its sequence is according to NCBI Reference Sequence NP_013828 or *S. cerevisiae* YMR110C.

As used herein, the terms "S-adenosylmethionine synthetase" and "SAM1" or "Sam1" refer to an encoding nucleic acid and an S-adenosylmethionine synthetase that catalyzes transfer of the adenosyl group of ATP to the sulfur atom of methionine. In certain embodiments, its EC number is 2.5.1.6. In certain embodiments, its sequence is according to GenBank locus AAB67461 or *S. cerevisiae* YLR180W.

As used herein, the terms "S-adenosylmethionine synthetase" and "SAM2" or "Sam2" or "ETH2" or "Eth2" refer to an encoding nucleic acid and an S-adenosylmethionine synthetase that catalyzes transfer of the adenosyl group of ATP to the sulfur atom of methionine. In certain embodiments, its EC number is 2.5.1.6. In certain embodiments, its sequence is according to NCBI Reference Sequence AAT93205.1 or *S. cerevisiae* YDR502C. Sam1 and Sam2 are paralogs and are identified by their abbreviations herein.

As used herein, the terms "S-adenosyl-L-homocysteine hydrolase" and "SAH1" or "Sah1" refer to an encoding nucleic acid and an S-adenosyl-L-homocysteine hydrolase that catabolizes S-adenosyl-L-homocysteine which is formed after donation of the activated methyl group of S-adenosyl-L-methionine (AdoMet) to an acceptor. In certain embodiments, its EC number is 3.3.1.1. In certain embodiments, its sequence is according to GenBank locus X07238 or *S. cerevisiae* YER043C.

As used herein, the terms "cobalamin-independent methionine synthase" and "MET6" or "Met6" refer to an encoding nucleic acid and a cobalamin-independent methionine synthase that is involved in methionine biosynthesis and regeneration and requires a minimum of two glutamates on the methyltetrahydrofolate substrate. In certain embodiments, its EC number is 2.1.1.14. In certain embodiments, its sequence is according to GenBank locus AY692801 or *S. cerevisiae* YER091C.

As used herein, the terms "cytosolic serine hydroxymethyltransferase" and "SHM2" or "Shm2" refer to an encoding nucleic acid and a cytosolic serine hydroxymethyltransferase that converts serine to glycine plus 5,10 methylenetetrahydrofolate. In certain embodiments, its EC number is 2.1.2.1. In certain embodiments, its sequence is according to GenBank locus AAB68164 or *S. cerevisiae* YLR058C.

As used herein, the term "MET12" or "Met12" refers to an encoding nucleic acid and an isozyme of methylenetetrahydrofolate reductase (MTHFR). In certain embodiments, its EC number is 1.5.1.20. In certain embodiments, its sequence is according to NCBI Reference Sequence NP_013159 or *S. cerevisiae* YPL023C.

As used herein, the term "MET13" or "Met13" refers to an encoding nucleic acid and an isozyme of methylenetetrahydrofolate reductase (MTHFR). In certain embodiments, its EC number is 1.5.1.20. In certain embodiments, its sequence is according to GenBank locus Z72647 or *S. cerevisiae* YGL125W.

As used herein, the terms "dihydrofolate reductase" and "DHFR" refer to an encoding nucleic acid and a dihydrofolate reductase. In certain embodiments, its EC number is 1.5.1.3. In certain embodiments, DHFR is from *Mus musculus*. In certain embodiments, the DHFR sequence is according to NCBI reference sequence NP_034179.

As used herein, the terms "3-dehydroquinate synthase" and "AroB" refer to an encoding nucleic acid and a 3-dehydroquinate synthase. In certain embodiments, its EC number is 4.2.3.4. In certain embodiments, AroB is from *E. coli*. In certain embodiments, the AroB sequence is according to UniProtKB P07639.

As used herein, the terms "3-dehydroquinate dehydratase" and "AroD" refer to an encoding nucleic acid and a 3-dehydroquinate dehydratase. In certain embodiments, its EC number is 4.2.1.10. In certain embodiments, AroD is from *E. coli*. In certain embodiments, the AroD sequence is according to UniProtKB P05194.

As used herein, the terms "phospho-2-dehydro-3-deoxyheptonate aldolase, Tyr-sensitive" and "AroF" refer to an encoding nucleic acid and a phospho-2-dehydro-3-deoxyheptonate aldolase. In certain embodiments, its EC number is 2.5.1.54. In certain embodiments, AroF is from *E. coli*. In certain embodiments, the AroF sequence is according to UniProtKB P00888. In certain embodiments, the AroF is feedback resistant (*J. Bacteriol*. November 1990 172:6581-6584).

As used herein, the terms "3-dehydroshikimate dehydratase" and "AroZ" refer to an encoding nucleic acid and a 3-dehydroshikimate (3-DHS) dehydratase. In certain embodiments, its EC number is 4.2.1.118. In certain embodiments, AroZ is from *Podospora pauciseta*. In certain embodiments, the AroZ sequence is according to Hansen et al., *Appl Environ Microbiol.* 2009 (May) 75(9):2765-74.

As used herein, the terms "phosphopantetheinyl transferase" and "PPTASE" refer to an encoding nucleic acid and a phosphopantetheinyl transferase. In certain embodiments, its EC number is 2.7.8.7. In certain embodiments, PPTASE is from *Corynebacterium glutamicum*. In certain embodiments, the PPTASE sequence is according to UniProtKB Q8NP45.

As used herein, the terms "aromatic carboxylic acid reductase" and "ACAR" refer to an encoding nucleic acid and an aromatic carboxylic acid reductase. In certain embodiments, its EC number is 1.2,1.30.

As used herein, the terms "O-methyl transferase" and "OMT" refer to an encoding nucleic acid and an O-methyl transferase.

As used herein, the terms "eugenol alcohol oxidase" and "EAO" refer to an encoding nucleic acid and a eugenol alcohol oxidase. In certain embodiments, EAO is from *Rhodococcus jostii*. In certain embodiments, the EAO sequence is according to UniProtKB Q0SBK1.

As used herein, the terms "UDP-glycosyltransferase" and "UGT" refer to an encoding nucleic acid and a UDP-glycosyltransferase. In certain embodiments, its EC number is 2.4.1.126. In certain embodiments, the UGT is from *Arabidopsis thaliana*. In certain embodiments, the UGT is *A. thaliana* UGT72E2. In certain embodiments, the UGT sequence is according to UniProtKB Q9LVR1.

As used herein, the term "parent cell" refers to a cell that has an identical genetic background as a genetically modified cell strain disclosed herein except that it does not comprise one or more particular genetic modifications engineered into the modified cell strain. In some embodiments, one or more particular genetic modifications are selected from the group consisting of: heterologous expression of an enzyme of a vanillin pathway, heterologous expression of an enzyme of a glucovanillin pathway; or heterologous expression of SAM1, SAM2, SAH1, MET6, SHM2, MET12, MET13, a MET13 chimera, AroB, AroD, AroF, AroZ, PPTASE, ACAR, OMT, EAO, or UGT.

As used herein, the term "naturally occurring" refers to what is found in nature. For example, gene product that is present in an organism that can be isolated from a source in nature and that has not been intentionally modified by a human in the laboratory is naturally occurring gene product. Conversely, as used herein, the term "non-naturally occurring" refers to what is not found in nature and is created by human intervention. In certain embodiments, naturally occurring genomic sequences are modified, e.g. codon optimized, for use in the organisms provided herein, and the resulting modified organisms expressing the modified (recombinant or heterologous) sequence is a non-naturally occurring (heterologous) organism, and the modified sequence is a non-naturally occurring (recombinant or heterologous) sequence (e.g. nucleic acid).

The term "medium" refers to a culture medium and/or fermentation medium.

The term "fermentation composition" refers to a composition that comprises one or more genetically modified cell strains and products or metabolites produced by the genetically modified cell strains. An example of a fermentation composition is a whole cell broth, which may be the entire contents of a vessel (e.g., a flasks, plate, or fermentor), including cells, aqueous phase, and compounds produced from the genetically modified cell strains. A fermentation composition includes the cell broth (i.e., culture medium), the cultured cell strain or strains (e.g., one or more yeast strains), and any compounds or molecules in the broth medium at any point in time during the culturing of the cell strain(s). The fermentation composition may be the entire contents or some of the contents of the whole cell broth.

As used herein, the term "production" generally refers to an amount of vanillin or a derivative thereof produced by a genetically modified cell strain provided herein. Derivatives can include glucovanillin, vanillyl alcohol, and/or vanillic acid. In some embodiments, production is expressed as a yield of vanillin or glucovanillin by the cell strain. In other embodiments, production is expressed as the productivity of the cell strain in producing the vanillin or glucovanillin.

As used herein, the term "productivity" refers to production of a vanillin or a derivative thereof by a cell strain, expressed as the amount of vanillin or glucovanillin produced (by weight) per amount of fermentation broth in which the cell strain is cultured (by volume) over time (per hour). Derivatives can include glucovanillin, vanillyl alcohol, and/or vanillic acid.

As used herein, the term "yield" refers to production of a vanillin or a derivative thereof by a cell strain, expressed as the amount of vanillin or glucovanillin produced per amount of carbon source consumed by the cell strain, by weight. Derivatives can include glucovanillin, vanillyl alcohol, and/or vanillic acid.

As used herein, the term "titer" refers to production of a vanillin or a derivative thereof by a cell strain, expressed as the amount of vanillin or glucovanillin or other derivative produced per volume of media. Derivatives can include glucovanillin, vanillyl alcohol, and/or vanillic acid.

As used herein, the term "an undetectable level" of a compound (e.g., vanillic acid, or other compounds) means a level of a compound that is too low to be measured and/or analyzed by a standard technique for measuring the compound. For instance, the term includes the level of a compound that is not detectable by the typical analytical methods known in the art.

The term "vanillin" refers to the compound vanillin, including any stereoisomer of vanillin. The chemical name of vanillin is 4-hydroxy-3-methoxybenzaldehyde. In particular embodiments, the term refers to the compound according to the following structure:

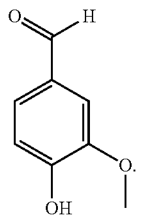

The term "vanillyl alcohol" refers to the compound vanillyl alcohol, including any stereoisomer of vanillyl alcohol. The chemical name of vanillyl alcohol is 4-(hydroxymethyl)-2-methoxyphenol. In particular embodiments, the term refers to the compound according to the following structure:

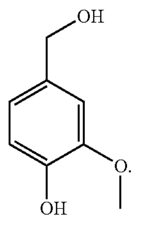

The term "vanillic acid" refers to the compound vanillic acid, including any stereoisomer of vanillic acid. The chemical name of vanillic acid is 4-hydroxy-3-methoxybenzoic acid. In particular embodiments, the term refers to the compound according to the following structure:

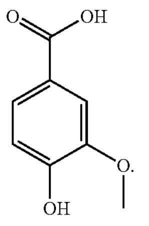

The term "glucovanillin" refers to the compound glucovanillin, including any stereoisomer of glucovanillin. The chemical name of glucovanillin is 3-methoxy-4-[(2S,3R,4S,5S,6R)-3,4,5-trihydroxy-6-(hydroxymethyl)oxan-2-yl]oxybenzaldehyde. In particular embodiments, the term refers to the compound according to the following structure:

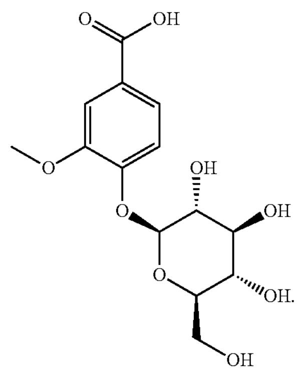 [SMILES: COc1cc(C(=O)O)ccc1O[C@@H]1O[C@H](CO)[C@@H](O)[C@H](O)[C@H]1O]

The term "protecatechuic acid" refers to the compound protecatechuic acid, including any stereoisomer of protecatechuic acid. The chemical name of protecatechuic acid is 3,4-dihydroxybenzoic acid. In particular embodiments, the term refers to the compound according to the following structure:

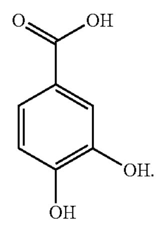 [SMILES: O=C(O)c1ccc(O)c(O)c1]

As used herein, the term "variant" refers to a polypeptide differing from a specifically recited "reference" polypeptide (e.g., a wild-type sequence) by amino acid insertions, deletions, mutations, and/or substitutions, but retains an activity that is substantially similar to the reference polypeptide. In some embodiments, the variant is created by recombinant DNA techniques or by mutagenesis. In some embodiments, a variant polypeptide differs from its reference polypeptide by the substitution of one basic residue for another (i.e. Arg for Lys), the substitution of one hydrophobic residue for another (i.e. Leu for Ile), or the substitution of one aromatic residue for another (i.e. Phe for Tyr), etc. In some embodiments, variants include analogs wherein conservative substitutions resulting in a substantial structural analogy of the reference sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

As used herein, the term "sequence identity" or "percent identity," in the context or two or more nucleic acid or protein sequences, refers to two or more sequences or subsequences that are the same or have a specified percentage of amino acid residues or nucleotides that are the same. For example, the sequence can have a percent identity of at least 60%, at least 65%, at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer programs and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.,* 22: 4673-4680), ALIGN (Myers et al., (1988) *CABIOS,* 4: 11-17), FASTA (Pearson et al., (1988) *PNAS,* 85:2444-2448; Pearson (1990), *Methods Enzymol.,* 183: 63-98) and gapped BLAST (Altschul et al., (1997) *Nucleic Acids Res.,* 25: 3389-3402) are useful for this purpose. The BLAST or BLAST 2.0 (Altschul et al., *J. Mol. Biol.* 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=2, Nucleic mismatch=−3, Expectation value=10.0, Word size=11, Max matches in a query range=0). For polypeptide sequence alignment and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0). Alternatively, the following program and parameters can be used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix. In the embodiments described herein, the sequence identity is calculated using BLASTN or BLASTP programs using their default parameters. In the embodiments described herein, the sequence alignment of two or more sequences are performed using Clustal W using the suggested default parameters (Dealign input sequences: no; Mbed-like clustering guide-tree: yes; Mbed-like clustering iteration: yes; number of combined iterations: default (0); Max guide tree iterations: default; Max HMM iterations: default; Order: input).

Fermentation Compositions

In one aspect, provided herein are fermentation compositions comprising an increased amount of p-aminobenzoic acid along with one or more cell strains capable of producing vanillin and/or glucovanillin. As shown in the Examples herein, increased amounts of p-aminobenzoic acid can provide increased yields and/or productivities of vanillin or glucovanillin from producing strains. Useful cell strains are described in the sections below.

The p-aminobenzoic acid can be prepared by standard techniques or obtained by commercial sources. The amount of p-aminobenzoic acid can be any amount deemed suitable to increase vanillin or glucovanillin yield or productivity, or both, deemed suitable by the practitioner of skill. In certain embodiments, the fermentation composition comprises about 1 mg/L to about 50 mg/L p-aminobenzoic acid. In certain embodiments, the fermentation composition comprises about 1 mg/L to about 45 mg/L p-aminobenzoic acid. In certain embodiments, the fermentation composition comprises about 1 mg/L to about 40 mg/L p-aminobenzoic acid. In certain embodiments, the fermentation composition comprises about 1 mg/L to about 35 mg/L p-aminobenzoic acid. In certain embodiments, the fermentation composition comprises about 1 mg/L to about 30 mg/L p-aminobenzoic acid. In certain embodiments, the fermentation composition comprises about 1 mg/L to about 25 mg/L p-aminobenzoic acid. In certain embodiments, the fermentation composition comprises about 2 mg/L to about 30 mg/L p-aminobenzoic acid. In certain embodiments, the fermentation composition comprises about 3 mg/L to about 30 mg/L p-aminobenzoic acid. In certain embodiments, the fermentation composition comprises about 4 mg/L to about 30 mg/L p-aminobenzoic acid. In certain embodiments, the fermentation composition comprises about 5 mg/L to about 30 mg/L p-aminobenzoic acid The fermentation compositions may further comprise a medium. Useful media and conditions are described in the section below. In certain embodiments, the fermentation compositions further comprise vanillin or glucovanillin. In certain embodiments, the fermentation compositions provided herein comprise vanillin as a major component of the vanillin and/or glucovanillin produced from the genetically modified cell strain. In certain embodiments, the fermentation compositions provided herein comprise glucovanillin as a major component of the vanillin and/or glucovanillin produced from the genetically modified cell strain.

Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the cell strain, the fermentation, and the process.

The methods of producing vanillin and/or glucovanillin provided herein may be performed in a suitable culture medium in a suitable container, including but not limited to a cell culture plate, a microtiter plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the cell strain, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a cell strain capable of producing vanillin or glucovanillin can subsist, i.e., maintain growth and viability. In some embodiments, the culture medium is an aqueous medium comprising assimilable carbon, nitrogen, and phosphate sources. Such a medium can also include appropriate salts, minerals, metals, and other nutrients. In some embodiments, the carbon source and some or all of the essential cell nutrients are added incrementally or continuously to the fermentation media. In certain embodiments, a subset of the essential nutrients are maintained in excess, while a few required nutrients, e.g., one or two, are maintained at about the minimum levels needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate, ethanol, and glycerol.

The concentration of a carbon source, such as glucose, in the culture medium is sufficient to promote cell growth, but is not so high as to repress growth of the microorganism used. Typically, cultures are run with a carbon source, such as glucose, being added at levels to achieve the desired level of growth and biomass. In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts, and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals, or growth promoters. Such other compounds can also be present in carbon, nitrogen, or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

The culture medium can also contain a suitable sulfur source. Preferred sulfur sources include, but are not limited to, sulfate salts such as ammonium sulfate ($(NH_4)_2SO_4$), magnesium sulfate ($MgSO_4$), potassium sulfate ($K_2SO_4$), and sodium sulfate ($Na_2SO_4$) and mixtures thereof. Typically, the concentration of sulfate in the culture medium is greater than about 1.0 g/L, preferably greater than about 3.0 g/L and more preferably greater than about 10.0 g/L. Beyond certain concentrations, however, the addition of sulfate to the culture medium is not advantageous for the growth of the microorganisms. Accordingly, the concentration of sulfate in the culture medium is typically less than about 50 g/L, preferably less than about 30 g/L and more preferably less than about 20 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid, and mixtures thereof. Biologically acceptable bases include, but are not limited to, ammonium hydroxide, sodium hydroxide, potassium hydroxide, and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture during the production stage of the fermentation. In some embodiments, the culture may be supplemented with relatively high concentrations of such components at the outset, for example, of the production stage, so that growth and/or vanillin or glucovanillin production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of vanillin or glucovanillin. For example, prior to inoculation of the culture medium with an inoculum, the culture medium can be brought to and maintained at a temperature in the range of from about 20° C. to about 45° C., preferably to a temperature in the range of from about 25° C. to about 40° C. In certain embodiments, the cells are eukaryotic, e.g. yeast, and the temperature is in the range of from about 28° C. to about 34° C. In certain embodiments, the cells are prokaryotic, e.g. bacteria, and the temperature is in the range of from about 35° C. to about 40° C., for instance 37° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0. In certain embodiments, the cells are eukaryotic, e.g. yeast, and the pH is preferably from about 4.0 to about 6.5. In certain embodiments, the cells are prokaryotic, e.g. bacteria, and the pH is from about 6.5 to about 7.5, e.g. about 7.0.

In some embodiments, the carbon source concentration, such as the glucose, fructose or sucrose, concentration, of the culture medium is monitored during culture. Carbon source concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. The carbon source concentration is typically maintained below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose, fructose, or sucrose is used as a carbon source the glucose, fructose, or sucrose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a carbon source solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

Other suitable fermentation medium and methods are described in, e.g., WO 2016/196321.

Recovery of Vanillin and/or Glucovanillin

Once the vanillin or glucovanillin is produced by the cell strain, it may be recovered or isolated for subsequent use using any suitable separation and purification methods known in the art. In some embodiments, a clarified aqueous phase comprising the vanillin or glucovanillin is separated from the fermentation by centrifugation or filtration. In certain embodiments, flocculants and coagulants are added to the clarified aqueous phase, for instance, to the clarified aqueous phase.

The vanillin or glucovanillin produced in these cells may be present in the culture supernatant and/or associated with the cell strains. In embodiments where some of the vanillin or glucovanillin is associated with the cell strain, the recovery of the vanillin or glucovanillin may comprise a method of improving the release of the vanillin and/or glucovanillin from the cells. In some embodiments, this could take the form of washing the cells with hot water or buffer treatment, with or without a surfactant, and with or without added buffers or salts. In some embodiments, the temperature is any temperature deemed suitable for releasing the vanillin and/or glucovanillin. In some embodiments, the temperature is in a range from 40 to 95° C.; or from 60 to 90° C.; or from 75 to 85° C. In some embodiments, the temperature is 40, 45, 50, 55, 65, 70, 75, 80, 85, 90, or 95° C. In some embodiments physical or chemical cell disruption is used to enhance the release of vanillin and/or glucovanillin from the cell strain. Alternatively and/or subsequently, the vanillin or glucovanillin in the culture medium can be recovered using an isolation unit operations including, but not limited to solvent extraction, membrane clarification, membrane concentration, adsorption, chromatography, evaporation, chemical derivatization, crystallization, and drying.

Methods of Producing Vanillin or Glucovanillin

In another aspect, provided herein is a method for the production of a vanillin or glucovanillin, the method comprising the steps of: (a) culturing a population of any of the cell strains cells described herein that are capable of producing a vanillin or glucovanillin in a fermentation composition described herein suitable for making the vanillin or glucovanillin compound; and (b) recovering said vanillin or glucovanillin compound from the medium. Those of skill will recognize that the amount of a compound produced can be evaluated by measuring the amount of the compound itself, or more preferably the amount of the compound and derivatives of the compound. For instance, the amount of vanillin produced can be evaluated from the total amount of vanillin, vanillyl alcohol, glucovanillin, and glucovanillyl alcohol produced.

In some embodiments, the fermentation composition produces an increased amount of the vanillin or glucovanillin, or derivative thereof such as vanillyl alcohol or glucovanillyl alcohol, compared to a conventional fermentation composition without additional p-aminobenzoic acid. In some embodiments, the increased amount is at least 1%, 5%, 10%, 15%, 20%, or 25%, or greater than 25%, as measured, for example, in yield, production, and/or productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the cell strain produces an elevated level of a vanillin or glucovanillin, or derivative thereof such as vanillyl alcohol or glucovanillyl alcohol that is greater than about 0.25 grams per liter of fermentation medium. In some embodiments, the cell strain produces an elevated level of a vanillin or glucovanillin, or derivative thereof such as vanillyl alcohol or glucovanillyl alcohol that is greater than about 0.5 grams per liter of fermentation medium. In some embodiments, the cell strain produces an elevated level of a vanillin or glucovanillin, or derivative thereof such as vanillyl alcohol or glucovanillyl alcohol that is greater than about 0.75 grams per liter of fermentation medium. In some embodiments, the cell strain produces an elevated level of a vanillin or glucovanillin, or derivative thereof such as vanillyl alcohol or glucovanillyl alcohol, that is greater than about 1 grams per liter of fermentation medium. In some embodiments, the cell strain produces an elevated level of a vanillin or glucovanillin, or derivative thereof such as vanillyl alcohol or glucovanillyl alcohol that is greater than about 5 grams per liter of fermentation medium. In some embodiments, the cell strain produces an elevated level of a vanillin or glucovanillin, or derivative thereof such as vanillyl alcohol or glucovanillyl alcohol that is greater than about 10 grams per liter of fermentation medium. In some embodiments, the vanillin or glucovanillin, or one or more derivatives thereof, such as vanillyl alcohol or glucovanillyl alcohol, is produced in an amount from about 10 to about 50 grams, from about 10 to about 15 grams, more than about 15 grams, more than about 20 grams, more than about 25 grams, or more than about 30 grams per liter of cell culture.

In some embodiments, the cell strain produces an elevated level of a vanillin or glucovanillin, or derivative thereof such as vanillyl alcohol or glucovanillyl alcohol, that is greater than about 50 milligrams per gram of dry cell weight. In some such embodiments, the vanillin or glucovanillin, or one or more derivatives thereof, such as vanillyl alcohol or glucovanillyl alcohol, is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the cell strain produces an elevated level of a vanillin or glucovanillin, or one or more derivatives thereof, such as vanillyl alcohol or glucovanillyl alcohol, that is at least about 10%, at least about 15%, at least about 20%, or at least about 25% higher than the level of vanillin or glucovanillin, or derivative thereof such as vanillyl alcohol or glucovanillyl alcohol, produced by the same cell strain in a conventional fermentation composition, on a per unit volume of cell culture basis.

In some embodiments, the cell strain produces an elevated level of a vanillin or glucovanillin, or one or more derivatives thereof, such as vanillyl alcohol or glucovanillyl alcohol, that is at least about 10%, at least about 15%, at least about 20%, or at least about 25% higher than the level of vanillin or glucovanillin, or derivative thereof such as vanillyl alcohol or glucovanillyl alcohol, produced by the same cell strain in a conventional fermentation composition, on a per unit dry cell weight basis.

In some embodiments, the cell strain produces an elevated level of a vanillin or glucovanillin, or one or more derivatives thereof, such as vanillyl alcohol or glucovanillyl alcohol, that is at least about 10%, at least about 15%, at least about 20%, or at least about 25% higher than the level of vanillin or glucovanillin, or derivative thereof such as vanillyl alcohol or glucovanillyl alcohol, produced by the same cell strain in a conventional fermentation composition, on a per unit volume of cell culture per unit time basis.

In some embodiments, the cell strain produces an elevated level of a vanillin or glucovanillin, or one or more derivatives thereof, such as vanillyl alcohol or glucovanillyl alcohol, that is at least about 10%, at least about 15%, at least about 20%, or at least about 25% higher than the level of vanillin or glucovanillin, or derivative thereof such as vanillyl alcohol or glucovanillyl alcohol, produced by the same cell strain in a conventional fermentation composition, on a per unit dry cell weight per unit time basis.

In most embodiments, the production of vanillin or glucovanillin by the cell strain is inducible by the presence of an inducing compound or the absence of a repressing compound. Such a cell strain can be manipulated with ease in the absence of the inducing compound or the presence of the repressing compound. The inducing compound is then added, or the repressing compound is diminished, to induce the production of the elevated level of vanillin or glucovanillin by the cell strain. In other embodiments, production of the elevated level of vanillin or glucovanillin by the cell strain is inducible by changing culture conditions, such as, for example, the growth temperature, media constituents, and the like. In certain embodiments, the vanillin-producing enzymes are repressed by maltose during a growth phase of the cells, and the vanillin-producing enzymes are expressed during an expression phase of the fermentation. Useful promoters and techniques are described in US 2018/0171341 A1, incorporated by reference in its entirety.

Cell Strains

Cell strains useful compositions and methods provided herein include archae, prokaryotic, or eukaryotic cells.

Suitable prokaryotic cells include, but are not limited, to any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the cell strain is an *Escherichia coli* cell.

Suitable archae cells include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic cells include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the cell strain is *Saccharomyces cerevisiae, Pichia pastoris, Schizosaccharomyces pombe, Dekkera bruxellensis, Kluyveromyces lactis* (previously called *Saccharomyces lactis*), *Kluverornyces marxianus, Arxula adeninivorans*, or *Hansenula polyrnorpha* (now known as *Pichia angusta*). In some embodiments, the cell strain is of the genus *Candida*, such as *Candida lipolytica, Candida guilliermondii, Candida krusei, Candida pseudotropicalis*, or *Candida utilis*.

In a particular embodiment, the cell strain is *Saccharomyces cerevisiae*. In some embodiments, the cell strain is *Saccharomyces cerevisiae* selected from the group consisting of Baker's yeast, CEN.PK, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the cell strain is *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, high pressure, expanded substrate utilization, nutrient limitation, osmotic stress due to sugar and salts, acidity, sulfite and bacterial contamination, or combinations thereof, which are recognized stress conditions of the industrial fermentation environment.

Genetically Modified Cell Strains

The cell strains can be any cell strains that produce vanillin or glucovanillin deemed suitable by the practitioner of skill. In certain embodiments, provided herein are cell strains comprising one or more enzymes useful for the production of vanillin and/or glucovanillin. In certain embodiments, provided herein are cell strains comprising one or more deletions in genes wherein the one or more deletions are useful for the production of vanillin and/or glucovanillin. In a further aspect, provided herein are cell strains that comprise one or more of the deletions and further comprise one or more of the enzymes. The enzymes and deletions are described in detail herein. In certain embodiments, the cell strains can produce vanillin and/or glucovanillin from a carbon source in a culture medium. In certain embodiments, the cell strains provide improved yield and/or productivity compared to a parent strain. In certain embodiments, the cell strains provide byproducts, intermediates, and/or side products, e.g. vanillic acid, compared to a parent strain. Exemplary byproducts, intermediates, and/or side products include vanillic acid, vanillyl alcohol, glucovanillic acid, glucovanillyl alcohol, and protocatechuic aldehyde.

In advantageous embodiments, the cell strain comprises one or more enzymatic pathways capable of making vanillin and/or glucovanillin, said pathways taken individually or together.

In another aspect, provided herein are cell strains that express one or more heterologous O-methyltransferases (OMTs). As shown in FIG. 1, OMT catalyzes the conversion of protocatechuic acid (PCA) to vanillic acid and the conversin of PC aldehyde to vanillin. The OMT can be any OMT deemed useful by those of skill. In advantageous embodiments, the OMT has specificity for the correct —OH group of protocatechuic acid. In other words, in advantageous embodiments, the OMT forms more vanillic acid and less side product in this reaction. As described herein, these OMTs provide excellent specificity for the correct —OH group and minimize formation of side product. In certain embodiments, the cell strains express one or more OMTs selected from the group consisting of OMTs from the following organism sources: *Brachypodium distachyon, Brassica napus, Chelonia mydas, Cicer arietinum, Ciona intestinalis, Coccidioides posadasii, Cucumis sativus, Danio rerio, Dicentrarchus labrax, Esox lucius, Hordeum vulgare, Ictalurus punctatus, Medicago truncatula, Oryzias latipes, Osmerus mordax, Phoenix dactylifera, Setaria italica, Solanum tuberosum, Sorghum bicolor, Streptomyces* sp. Root431, and *Tuber melanosporum.*

In further embodiments, the above cell strains further comprise one or more deletions and/or one or more expressed genes useful for the production of vanillin and/or glucovanillin.

In particular embodiments, the cell strains further comprise enzymes of a pathway useful for the production of vanillin or glucovanillin. Such pathway enzymes have been described previously, including those described in Hansen et al., *Appl. Environ. Microbiol.* (2009) 75(9):2765-2774; U.S. Pat. Nos. 6,372,461 B1; 10,066,252 B1; 10,208,293 B2; each of which are incorporated by reference in their entireties.

In certain embodiments, the cell strains further comprise a 3-dehydroquinate synthase, or AroB. Useful AroB genes and enzymes are known. Useful AroB polypeptides are also known. Useful AroB genes and enzymes include those of *E. coli*. Examples can be found at UniProtKB P07639. In preferred embodiments, the cell strains further express or overexpress *E. coli* AroB.

In certain embodiments, the cell strains further comprise a 3-dehydroquinate dehydratase, or AroD. Useful AroD genes and enzymes are known. Useful AroD polypeptides are also known. Useful AroD genes and enzymes include those of *E. coli*. Examples can be found at UniProtKB P05194. In preferred embodiments, the cell strains further express or overexpress *E. coli* AroD.

In certain embodiments, the cell strains further comprise a phospho-2-dehydro-3-deoxyheptonate aldolase, Tyr-sensitive, or AroF. Useful AroF genes and enzymes are known. Useful AroF polypeptides are also known. Useful AroF genes and enzymes include those of *E. coli*. Examples can be found at UniProtKB P00888. In preferred embodiments, the cell strains further express or overexpress *E. coli* AroF. In certain embodiments, the AroF is feedback resistant (*J. Bacteriol. November* 1990 172:6581-6584, incorporated by reference in its entirety).

In certain embodiments, the cell strains further comprise a 3-dehydroshikimate dehydratase, or AroZ. Useful AroZ genes and enzymes are known. Useful 3DSD polypeptides are also known. Useful AroZ genes and enzymes include those of *Podospora pauciseta, Ustilago maydis, Rhodoicoccus jostii, Acinetobacter* sp., *Aspergillus niger* and *Neurospora crassa*. Examples can be found at GenBank Accession Nos. CAD60599, XP_001905369.1, XP_761560.1, ABG93191.1, AAC37159.1, and XM_001392464. In preferred embodiments, the cell strains further express or overexpress Podospora pauciseta AroZ.

In certain embodiments, the cell strains further comprise an ACAR. Useful ACAR genes and enzymes are known. Useful ACAR polypeptides are also known. In certain embodiments, the cell strains express one or more ACAR enzymes from one or more of the following organism sources: *Actinokineospora spheciospongiae, Aspergillus terreus, Coccomyxa subellipsoidea, Gordonia effusa, Hypocrea jecorina, Kibdelosporangium* sp. MJ126-NF4, *Lichtheimia corymbifera, Metarhizium brunneum, Mycobacterium abscessus, Mycobacterium avium, Mycobacterium cosmeticum, Mycobacterium lepromatosis, Mycobacterium nebraskense, Mycobacterium obuense, Mycobacterium* sp. MOTT36Y, *Mycobacterium* sp. URHB0044, *Mycobacterium vaccae, Mycobacterium xenopi, Neurospora crassa, Nocardia brasiliensis, Nocardia gamkensis, Nocardia iowensis, Nocardia otitidiscaviarum, Nocardia seriolae, Nocardia terpenica, Nocardia vulneris, Purpureocillium lilacinum, Rhodococcus* sp. Leaf258, *Streptomyces* sp. NRRL S-31, *Talaromyces marneffei.*

In certain embodiments, the cell strains further comprise a PPTASE. Useful PPTASE genes and enzymes are known. Useful PPTASE polypeptides are also known. Useful PPTASE genes and enzymes include those of *E. coli, Corynebacterium glutamicum*, and *Nocardia farcinica*. Examples can be found at GenBank Accession Nos. NP_601186, BAA35224, and YP_120266. In preferred embodiments, the cell strains further express or overexpress *Cornybacterium glutamicum* PPTASE.

In certain embodiments, the cell strains are capable of converting vanillyl alcohol to vanillin. This reduces the amount of the side product vanillyl alcohol and increases the amount of vanillin. Useful oxidase genes and enzymes are known. Suitable oxidase polypeptides are known. Useful oxidase genes and enzymes include those of *Penicillium*

*simplicissimum* and *Rhodococcus jostii*. In preferred embodiments, the cell strains further express or overexpress *Rhodococcus jostii* eugenal alcohol oxidase (EAO).

In certain embodiments, the cell strains are capable of glucosylating vanillin to form glucovanillin. Glucovanillin is a storage form of vanillin found in the vanilla pod. It is non-toxic to most organisms, including yeast, and has a higher solubility in water, as compared to vanillin. In addition, the formation of vanillin-β-D-glucoside most likely directs biosynthesis toward vanillin production. Useful UGT genes and enzymes for this conversion are known. Useful UGT enzymes according to the invention are classified under EC 2.4.1. Suitable UGT polypeptides include the UGT71C2, UGT72B1, UGT72E2, UGT84A2, UGT89B1, UGT85B1, and arbutin synthase polypeptides, at, for example, GenBank Accession Nos. AC0005496, NM_116337, and NM_126067. In certain embodiments, the cell strains further express or overexpress one or more of UGT71C2, UGT72B1, UGT72E2, UGT84A2, UGT89B1, UGT85B1, and arbutin synthase. In preferred embodiments, the cell strains further express or overexpress *A. thaliana* UGT72E2.

In one aspect, provided herein are cell strains that comprise deletion of HFD1. As described in the examples below, HFD1 encodes the enzyme Hfd1 which is capable of converting vanillin to vanillic acid. Since vanillic acid is potentially toxic to cell strains, and an undesired impurity in the final product, it is an undesired fermentation side product. Further, accumulation of vanillic acid can make purification more difficult. In addition, the reverse reaction of vanillin to vanillic acid can introduce a futile cycle between vanillic acid and vanillin. Each forward reaction of vanillic acid to vanillin costs valuable cellular ATP and NADPH, which would then be wasted by the subsequent conversion of vanillin back to vanillic acid. In certain embodiments, the cell strains are *S. cerevisiae*. As described in the examples below, Hfd1 is the primary known enzyme responsible for converting vanillin to vanillic acid in *S. cerevisiae*. In cell strains other than *S. cerevisiae*, a homolog of HFD1 is deleted. Preferably, all copies of HFD1 are deleted. For instance, in haploid cells with one copy of HFD1, that copy is deleted. In diploid cells with two copies of HFD1, both copies are deleted. In any cells with multiple copies of HFD1, each copy is preferably deleted. The HFD1 gene(s) can be deleted by any technique apparent to those of skill in the art. Useful techniques include those based on homologous recombination and polymerase chain reaction (PCR).

Overexpression can be according to any technique apparent to those of skill in the art. In certain embodiments, the genes are overexpressed from a promoter useful in the cell strain. In certain embodiments, the genes are overexpressed from a *S. cerevisiae* promoter. In certain embodiments, the promoter is selected from the group consisting of pPGK1, pTDH3, pENO2, pADH1, pTPI1, pTEF1, pTEF2, pTEF3, pGAL1, pGAL2, pGAL7, pGAL10, GAL1, pRPL3, pRPL15A, pRPL4, pRPL8B, pSSA1, pSSB1, pCUP1, pTPS1, pHXT7, pADH2, pCYC1, and pPDA1. In certain embodiments, the genes are overexpressed from a GAL promoter. In certain embodiments, the genes are overexpressed from a promoter selected from the group consisting of pGAL1, pGAL2, pGAL7, pGAL10, and variants thereof.

In certain embodiments, one, some, or all of the heterologous promoters in the cell strains are inducible. The inducible promoter system can be any recognized by those of skill in the art. In particular embodiments, the promoters are inducible by maltose. In an advantageous embodiment, the cell strains comprise a GAL regulon that is inducible by maltose. Examples of the Gal regulon which are further repressed or induced by a maltose are described in PCT Application Publications WO2015/020649, WO2016/210343, and WO2016210350, each of which is incorporated by reference in its entirety. In certain embodiment, a maltose switchable strain is built on top of a non-switchable strain by chromosomally integrating a copy of GAL80 under the control of a maltose-responsive promoter such as pMAL32. In certain embodiments, the GAL80 gene product is mutated for temperature sensitivity, e.g. to facilitate further control. In certain embodiments, the GAL80 gene product is fused to a temperature-sensitive polypeptide. In certain embodiments, the GAL80 gene product is fused to a temperature-sensitive DHFR polypeptide or fragment. Additional description of switchable farnesene producing switchable strains are described in U.S. Patent Application Publication No. US 2016/0177341 and PCT Application Publication No. WO 2016/210350, each of which is incorporated herein by reference in its entirety.

For each of the polypeptides and nucleic acids described above, the cell strains can comprise variants thereof. In certain embodiments, the variant can comprise up to 15, 10, 9, 8, 7, 6, 5, 4, 3, 2, or 1 amino acid substitutions relative to the relevant polypeptide. In certain embodiments, the variant can comprise up to 15, 10, 9, 8, 7, 6, 5, 4, 3, 2, or 1 conservative amino acid substitutions relative to the reference polypeptide. In certain embodiments, any of the nucleic acids described herein can be optimized for the cell strain, for instance codon optimized. Variants and optimization are described in detail below.

In certain embodiments, the additional enzymes are native, unless specified otherwise above. Native enzymes can be expressed from codon optimized nucleic acids. In advantageous embodiments, the additional enzymes are heterologous. In certain embodiments, two or more enzymes can be combined in one polypeptide.

Methods of Making Genetically Modified Cells

Cell strains can be obtained or produced by standard techniques. The cell strains can be genetically engineered to comprise one or more of the modifications described above, e.g., one or more nucleic heterologous nucleic acids and/or biosynthetic pathway enzymes, e.g., for a vanillin or glucovanillin compound. Expression of a heterologous enzyme in a cell strain can be accomplished by introducing into the cell strains a nucleic acid comprising a nucleotide sequence encoding the enzyme under the control of regulatory elements that permit expression in the cell strain. In some embodiments, the nucleic acid is an extrachromosomal plasmid. In other embodiments, the nucleic acid is a chromosomal integration vector that can integrate the nucleotide sequence into the chromosome of the cell strain. In other embodiments, the nucleic acid is a linear piece of double stranded DNA that can integrate via homology the nucleotide sequence into the chromosome of the cell strain.

Nucleic acids encoding these proteins can be introduced into the cell strain by any method known to one of skill in the art without limitation (see, for example, Hinnen et al. (1978) *Proc. Natl. Acad. Sci.* USA 75:1292-3; Cregg et al. (1985) *Mol. Cell. Biol.* 5:3376-3385; Goeddel et al. eds, 1990, Methods in Enzymology, vol. 185, Academic Press, Inc., C A; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al. , eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The amount of an enzyme in a cell strain may be altered by modifying the transcription of the gene that encodes the enzyme. This can be achieved, for example, by modifying the copy number of the nucleotide sequence encoding the enzyme (e.g., by using a higher or lower copy number expression vector comprising the nucleotide sequence, or by introducing additional copies of the nucleotide sequence into the genome of the cell strain or by deleting or disrupting the nucleotide sequence in the genome of the cell strain), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a cell strain may be altered by modifying the level of translation of an mRNA that encodes the enzyme. This can be achieved, for example, by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a cell strain can be altered in a number of ways. These include, but are not limited to, expressing a modified form of the enzyme that exhibits increased or decreased solubility in the cell strain, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a cell strain comprises one or more selectable markers useful for the selection of transformed cell strains and for placing selective pressure on the cell strain to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, $KAN^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin. The NAT1 gene product from *S. noursei* confers resistance to nourseothricin. The PAT gene product from *S. viridochromogenes* Tu94 confers resistance to bialophos. The AUR1-C gene product from *Saccharomyces cerevisiae* confers resistance to Auerobasidin A (AbA). The PDR4 gene product confers resistance to cerulenin. The SMR1 gene product confers resistance to sulfometuron methyl. The CAT gene product from Tn9 transposon confers resistance to chloramphenicol. The mouse dhfr gene product confers resistance to methotrexate. The HPH gene product of *Klebsiella pneumonia* confers resistance to Hygromycin B. The DSDA gene product of *E. coli* allows cells to grow on plates with D-serine as the sole nitrogen source. The $KAN^R$ gene of the Tn903 transposon confers resistance to G418. The SH BLE gene product from *Streptoalloteichus hindustanus* confers resistance to Zeocin (bleomycin). In some embodiments, the antibiotic resistance marker is deleted after the genetically modified cell strain disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified cell strain generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods and compositions of the disclosure; however, it will be recognized that absolute identity to such genes is not necessary. For example, changes in a particular gene or polynucleotide comprising a sequence encoding a polypeptide or enzyme can be performed and screened for activity. Typically, such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other cell strains can be readily determined using codon usage tables or can be performed using commercially available software, such as CodonOp (www.idtdna.com/CodonOptfrom) from Integrated DNA Technologies.

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum, Kluyveromyces* spp., including *K. thermotolerans, K. lactis*, and *K. marxianus, Pichia* spp., *Hansenula* spp., including *H. polymorpha, Candida* spp., *Trichosporon* spp., *Yamadazyma* spp., including *Y.* spp. *stipitis, Torulaspora pretoriensis, Issatchenkia orientalis, Schizosaccharomyces* spp., including *S. pombe, Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli, Zym hvomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous UDP glycosyltransferases, or any biosynthetic pathway genes, proteins, or enzymes. Techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology,* 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

EXAMPLES

Example 1

Yeast Transformation Methods

Each DNA construct is integrated into *Saccharomyces cerevisiae* (CEN.PK2) with standard molecular biology techniques in an optimized lithium acetate (LiAc) transformation. Briefly, cells are grown overnight in yeast extract peptone maltose (YPD, 1% yeast extract, 2% peptone, 2% maltose in distilled water) media at 30° C. with shaking (200 rpm), diluted to an $OD_{600}$ of 0.1 in 100 mL YPD, and grown to an $OD_{600}$ of 0.6-0.8. For each transformation, 5 mL of culture is harvested by centrifugation, washed in 5 mL of sterile water, spun down again, resuspended in 1 mL of 100 mM LiAc, and transferred to a microcentrifuge tube. Cells are spun down (13,000×g) for 30 seconds, the supernatant is removed, and the cells are resuspended in a transformation mix of 240 μL 50% PEG, 36 μL 1 M LiAc, 10 μL boiled salmon sperm DNA, and 74 μL of donor DNA. Following a heat shock at 42° C. for 40 minutes, cells are recovered overnight in YPD media before plating on selective media. DNA integration is confirmed by colony PCR with primers specific to the integrations.

Example 2

Generation of a Strain with High Flux to Glucovanillin

FIG. 1 shows an exemplary biosynthetic pathway to produce glucovanillin from central carbon metabolites erythrose-4-phosphate (E4P) and phosphoenylpyruvate (PEP). A glucovanillin production strain was created from a wild-type *Saccharomyces cerevisiae* strain (CEN.PK) by expressing heterologous genes from native GAL promoters. This strain comprised the following chromosomally integrated heterologous genes: AroF, AroB, AroD, AroZ, OMT, ACAR, PPTase, UGT, and EAO. The following subset of these genes include two chromosomally integrated copies: AroZ and UGT. The following subset of these genes include four chromosomally integrated copies: OMT.

Example 3

Yeast Culturing Conditions in 96-Well Plates

Yeast colonies were picked into 96-well microtiter plates containing Bird Seed Media (BSM) 100 ml/L Bird Batch (Potassium phosphate 80 g/L, Ammonium Sulfate 150 g/L, and Magnesium Sulfate 61.5 g/L), 5 ml/L Trace Metal Solution (0.5M EDTA 160 mL/L, Zinc sulfate heptahydrate 11.5 g/L, Copper Sulfate 0.64 g/L, Manganese(II) chloride 0.64 g/L, Cobalt(II) Chloride Hexahydrate 0.94 g/L, Sodium molybdate 0.96 g/L, Iron(II) sulfate 5.6 g/L, and Calcium Chloride dihydrate 5.8 g/L), 12 mL/L Birds Vitamins 2.0 (Biotin 0.05 g/L, p-Aminobenzoic Acid 0.2 g/L, D-Pantothenic Acid 1 g/L, Nicotinic Acid 1 g/L, Myoinositol 25 g/L, Thiamine HCl 1 g/L, Pyridoxine HCl 1 g/L, Succinic Acid 6 g/L, and 1 g/L Lysine) with 1.9% Maltose and 0.1% Glucose. Cells were cultured at 30° C. in a high capacity microtiter plate incubator shaking at 1000 rpm and 80% humidity for 3 days until the cultures reached carbon exhaustion. The growth-saturated cultures were subcultured into fresh plates containing BSM with 4% sucrose and 1 g/L lysine by taking 14.4 μL, from the saturated cultures and diluting into 360 μL, of fresh media. Wells containing a reduced concentration of a nutrient were prepared with $1/50^{th}$ concentration compared to the base media. Cells in the production media were cultured at 30° C. in a high capacity microtiter plate shaker at 1000 rpm and 80% humidity for additional 3 days prior to extraction and analysis. Biomass density was measured by optical density at 600 nm.

Example 4

Quantification of Vanillin Y57481/Y57482

To quantify the amount of vanillin produced, the samples were first treated with a commercially available beta-glucosidase to convert glucovanillin into vanillin for analysis. Samples were then analyzed on a Agilent Vanquish™ Flex Binary UHPLC System with a diode array detector with the following program:

Mobile phase (A): 1.4% sulfuric acid v/v in water

Mobile phase (B): 100% acetonitrile

Gradient is as follows (gradient time, (min) mobile phase A, (%)): ((0.00, 88), (0.05, 88), (1.25, 85), (2.25, 83), (3.0, 82), (3.5, 88), (4.0, 88)). Flow rate was 1.

Example 5

Identification of Limiting Components in Yeast Growth Medium

Figure 2:
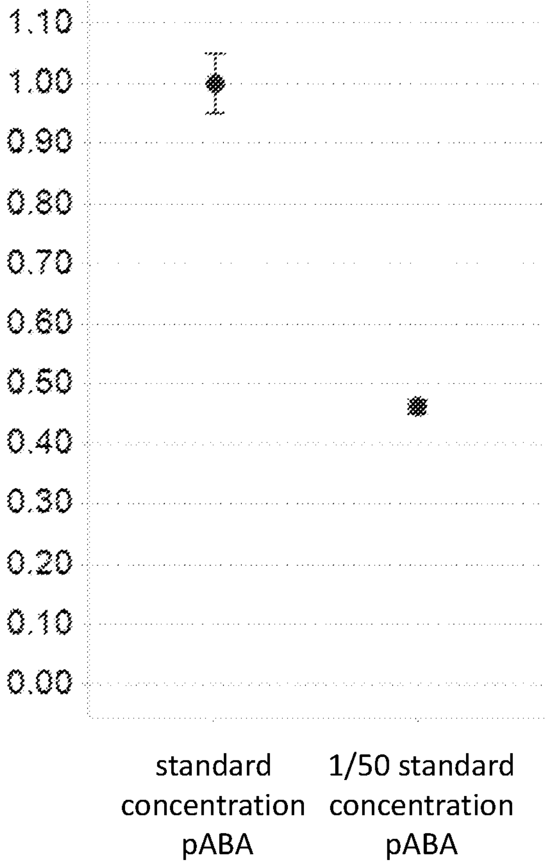
FIG. 2 is a graph providing relative titers of g/L Vanillin for a 96-well plate experiment using a vanillin producing strain in cultures comparing media containing standard pABA to media containing 1/50th standard amount of pABA. Strains were run as n=4, values were normalized by setting the highest data point for the standard concentration of pABA to a value of 1, and all other data points are relative fold increases or decreases normalized to that data point. The error bars represent 1 standard deviation from the mean.

Fermentation growth medium is comprised of a sugar source plus nutrients, vitamins and trace metals that the yeast cannot produce independently, or that enhance growth and production of the culture. Due to the high production of glucovanillin in our strains, the demand on primary metabolic pathways is different than that of a wild-type yeast culture. Therefore, it is plausible that the nutrient composition optimized for wild-type yeast may not be ideal for a glucovanillin producing culture. To determine whether a glucovanillin producing yeast strain as described above has a greater requirement for a trace media component compared to a nonproducer strain, media was prepared which reduced the concentration of one of the Trace Media Solution components to 1/50 of the standard concentration and growth of the culture was compared across samples for a nonproducer compared to a glucovanillin producer in 96-well plates. Results showed that reducing the concentration of para-aminobenzoic acid (pABA) resulted in the most significant reduction in glucovanillin production when the concentration of this nutrient in the media was reduced by $1/50^{th}$ compared to standard medium (FIG. 2).

Example 6

Fermentation Media and Conditions

A 0.5 ml of frozen cell suspension of a yeast strain containing the desired genetic modifications, was thawed and transferred into a 500-ml baffled flask containing 100 ml of BSM 3.5 (8 g/L $KH_2PO_4$, 7 g/L $(NH_4)_2SO_4$, 6.15 g/L $MgSO_4*7H_2O$, 3 mL/L 1×Bird Vitamins 3.5 (0.05 g/L biotin, 0.2 g/L p-aminobenzoic acid, 1 g/L nicotinic acid, 2.5 g/L myoinositol, 1 g/L pyridozine HCl, 1 g/L thiamine HCl, 1 g/L calcium pantothenate), 5 mL/L 1×Bird™ (5.75 g/L $ZnSO_4*7H_2O$, 0.32 g/L $CuSO_4$, 0.32 $MnCl_2*4H_2O$, 0.47 g/L $CoCl_2*6H_2O$, 0.48 g/L $Na_2MoO_4*2H_2O$, 2.8 g/L $FeSO_4*7H_2O$, 2.9 $CaCl_2*2H_2O$, 0.0585 EDTA) with 0.5M succinate buffer containing 2% sucrose, 4% maltose, and 5 g/L lysine. The cells were grown in a shaker at 28° C., 200 RPM for 21 hours.

A 0.25 mL aliquot of this culture was then transferred into a second flask containing 100 ml of BSM 3.5 containing 2% sucrose, 4% maltose, and 5 g/L lysine and grown in a shaker at 28° C., 200 RPM for 21 hours.

A 0.6 mL aliquot of this culture was then inoculated into a 0.5-L initial fermentor (IFA) containing 299.4 mL of IF media (8 g/L $KH_2PO_4$, 7 g/L $(NH_4)_2SO_4$, 6.15 g/L $MgSO_4*7H_2O$, 6 mL/L 4×Bird Vitamins 3.5 (0.2 g/L Biotin, 0.8 g/L p-aminobenzoic acid, 4 g/L nicotinic acid, 10 g/L myoinositol, 4 g/L pyridoxine HCl, 4 g/L thiamine HCl 4 g/L calcium pantothenate), 10 mL/L 2×Bird™ (1.5 g/L $ZnSO_4*7H_2O$, 0.64 g/L $CuSO_4$, 0.64 $MnCl_2*4H_2O$, 0.94 g/L $CoCl_2*6H_2O$, 0.96 g/L $Na_2MoO_4*2H_2O$, 5.6 g/L $FeSO_4*7H_2O$, 5.8 $CaCl_2*2H_2O$, 0.117 EDTA), 40 g/L Maltose, and 5 g/L Lysine). The nutrient feed to the IFA was concentrated pure sucrose delivered with an initial pulse equivalent to a 20 g TRS/L sugar. The IFA was operated at 28° C. for 24 hours.

60 mL of the IFA culture was then inoculated into a 0.5 L manufacturing fermentor (MFA) containing 240 mL of MF media (8 g/L $KH_2PO_4$, 7 g/L $(NH_4)2SO_4$, 6.15 g/L $MgSO_4*7H_2O$, 6 mL/L 4×Bird Vitamins 3.5, 10 mL/L 2×Bird™). To test the increased p-aminobenzoic acid (pABA) condition, the concentration of pABA was increased 5-fold from an initial concentration of 4.8 mg/L in the IF and MF fermentation media to 24 mg/L in the IF and MF fermentation media.

The nutrient feed to the fermentor was a defined sucrose feed delivered with an initial pulse of 10 g TRS/L (total reducing sugars per liter) sugar delivered at 1 g/L/h. The fermentor feed rate was then adjusted based on the culture demand for carbon, as indicated by rises in dissolved oxygen. The fermentation was run aerobically at a constant temperature of 30° C. and constant pH of 5.0 (controlled by ammonium hydroxide additions) until the dissolved oxygen reached 0%. The agitation was then controlled in order to maintain an oxygen utilization rate of 110 mmol $O_2$/L/h for the remainder of the fermentation. Culture was removed daily for sampling and to prevent overflow. Salts, trace metals, and vitamins were also added daily. 0.1 mL L-61 antifoam was added to the fermentation media at the beginning and subsequently added as needed. The amount of gluco-vanillin produced and the total sugar consumed by the cells was monitored daily and the ratio of these two values (i.e., the product yield off of sugar) was determined for each 24 hour period. The fermentor was run for 7 days.

Example 7

Figure 3:
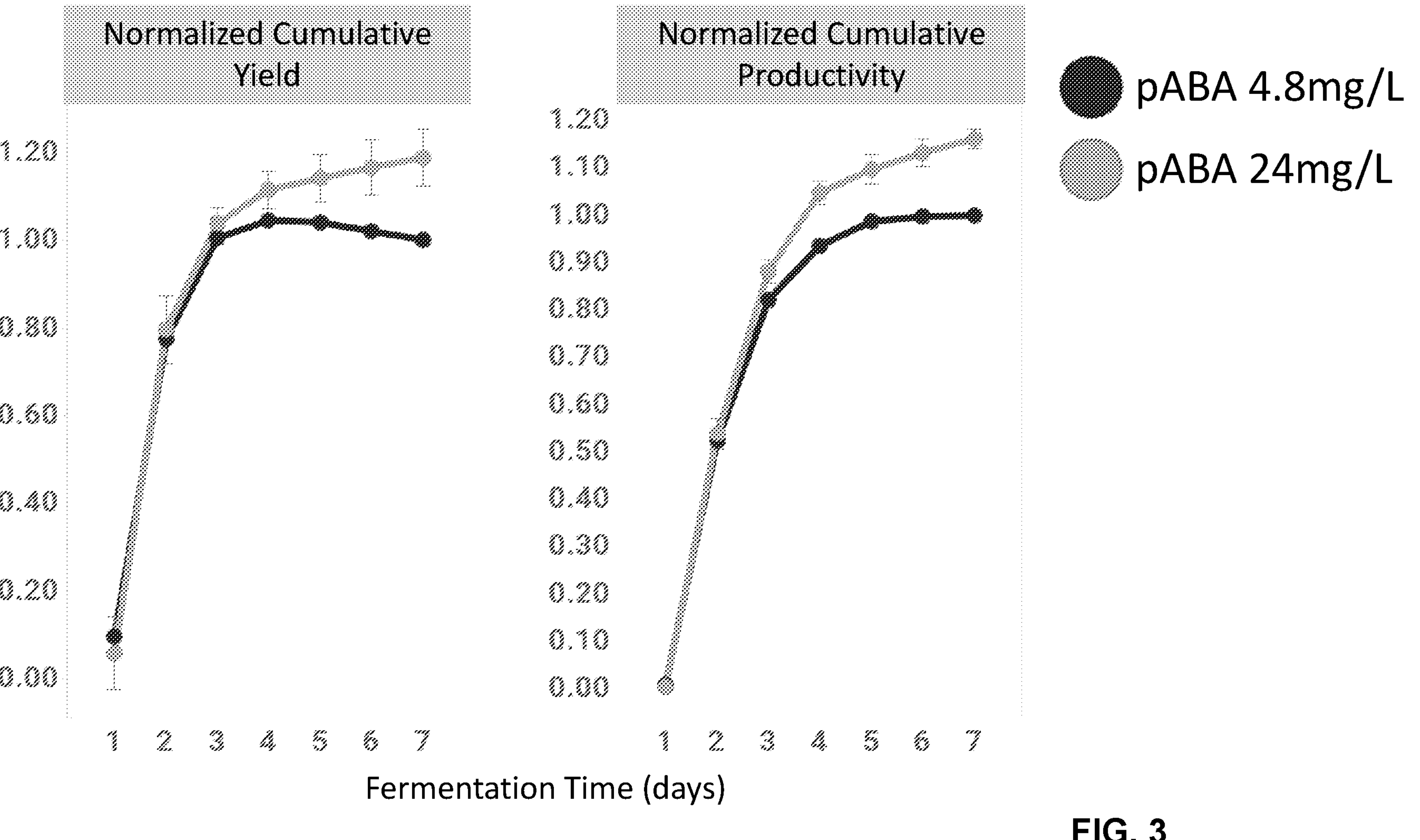
FIG. 3 is a graph providing relative Cumulative Yield (weight %; vanillin+vanillyl alcohol) and relative Cumulative Productivity (g/L/h; vanillin plus vanillyl alcohol) for a 7 day fermentation using a vanillin producing strain in cultures with 4.8 mg/L or 24 mg/L p-aminobenzoic acid. Cumulative indicates the value for the interval from time zero to the indicated time. Strains were run as n=2, the values were averaged and the error bars represent 1 standard deviation from the mean.

Increasing p-Aminobenzoic Acid Concentration in Fermentation Medium Improves Glucovanillin Production Cell density achieved in a high cell density continuous fermentation process is significantly higher than that achieved in a 96-well plate batch culture. Therefore to test whether glucovanillin strains, whose production was reduced by lowering the concentration of pABA in 96-well plate culture, could be improved by increasing the concentration of pABA in a high cell density fermentation, the concentration of pABA in the IF and MF fermentation media was increased by five-fold, and performance was compared to standard fermentation media. In the higher pABA condition, yield increased by 14% for a 7 day fermentation, and productivity increased by 13% for n=2 of each condition. Data is shown in FIG. 3.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A fermentation composition comprising:

(a) one or more genetically modified yeast cells capable of producing vanillin or glucovanillin, the one or more genetically modified yeast cells comprising:

(i) deletion of HFD1 gene; and (ii) one or more heterologous genes and/or overexpression of one or more genes selected from 3-dehydroquinate synthase (AroB), 3-dehydroquinate dehydratase (AroD), phospho-2-dehydro-3-deoxyheptonate aldolase (AroF), 3-dehydroshikimate dehydratase (AroZ), an O-methyl transferase (OMT) gene, a phosphopantetheinyl transferase (PPTASE) gene, an aromatic carboxylic acid reductase (ACAR) gene, eugenol alcohol oxidase (EAO) gene, and a UDP-glycosyltransferase (UGT) gene; and (b) about 24 to about 50 mg/L p-aminobenzoic acid.

2. The fermentation composition of claim 1, further comprising vanillin produced by the one or more yeast cells.

3. The fermentation composition of claim 1, further comprising glucovanillin produced by the one or more yeast cells.

4. The fermentation composition of claim 1, further comprising about 1% yeast extract, about 2% peptone, and about 2% dextrose.

5. The fermentation composition of claim 1, further comprising potassium phosphate, ammonium sulfate, magnesium sulfate, zinc sulfate, copper sulfate, magnesium chloride, cobalt chloride, sodium molybdate, iron sulphate, calcium chloride, biotin, nicotinic acid, myoinositol, pyridozine, thiamine, calcium pantothenate, and/or ethylenediametetraacetic acid (EDTA) in amounts suitable for growth of the one or more genetically modified yeast cells and production of the vanillin or glucovanillin.

6. The fermentation composition of claim 1, wherein the one or more genetically modified yeast cells comprise two chromosomally integrated copies of AroZ and UGT genes.

7. The fermentation composition of claim 1, wherein the one or more genetically modified yeast cells comprise four chromosomally integrated copies of an OMT gene and, optionally, wherein the one or more genetically modified yeast cells comprise two chromosomally integrated copies of AroZ and UGT genes.

8. The fermentation composition of claim 1, wherein the one or more heterologous genes and/or the one or more overexpressed genes are expressed from an inducible promoter.

9. The fermentation composition of claim 8, wherein the inducible promoter is a GAL promoter.

10. The fermentation composition of claim 8, wherein the one or more heterologous genes and/or the one or more overexpressed genes are expressed from a GAL promoter, and wherein a GAL80 gene is expression from a MAL promoter.

11. The fermentation composition of claim 1, wherein the one or more genetically modified yeast cells comprise one or more selected from the group consisting of *Saccharomyces cerevisiae, Pichia pastoris, Schizosaccharomyces pombe, Dekkera burxellensis, Kluveromyces lactis* (*Saccharomyces lactis*), *Kluveromyces maxianus, Arxula adeninvorans, Hansenula polymorpha* (*Pichia angusta*), *Candida lipolytica, Candida* guillermondii, *Candida kruseii, Candida pseudotropicalis*, and *Candida utilis*.

12. The fermentation composition of claim 1, wherein at least one of the one or more genetically modified yeast cells is *Saccharomyces cerevisiae.*

13. A method for producing vanillin or one or more glucovanillins comprising the steps:

(a) culturing the fermentation composition of claim 1 under conditions suitable for making vanillin or one or more glucovanillins to yield a culture broth; and (b) recovering said vanillin or one or more glucovanillins from the culture broth.

14. The method of claim 13, wherein at least one of the one or more genetically modified yeast cells is *Saccharomyces cerevisiae.*

* * * * *